US011628228B2

(12) United States Patent
Zhang et al.

(10) Patent No.: US 11,628,228 B2
(45) Date of Patent: Apr. 18, 2023

(54) $^{99m}$TC-LABELED ISONITRILE-CONTAINING GLUCOSE DERIVATIVE AND PREPARATION METHOD AND USE THEREOF

(71) Applicant: Beijing Shihong Pharmaceutical Research Center, Beijing (CN)

(72) Inventors: Junbo Zhang, Beijing (CN); Xuran Zhang, Beijing (CN); Qianqian Gan, Beijing (CN); Xin Shao, Beijing (CN); Xuebin Wang, Beijing (CN); Zhigang Tang, Beijing (CN); Jie Lu, Beijing (CN); Zhanbin Zhang, Beijing (CN)

(73) Assignee: Beijing Shihong Pharmaceutical Research Center, Beijing (CN)

( * ) Notice: Subject to any disclaimer, the term of this patent is extended or adjusted under 35 U.S.C. 154(b) by 616 days.

(21) Appl. No.: 16/310,909

(22) PCT Filed: Jan. 24, 2018

(86) PCT No.: PCT/CN2018/073950
§ 371 (c)(1),
(2) Date: Dec. 18, 2018

(87) PCT Pub. No.: WO2018/227977
PCT Pub. Date: Dec. 20, 2018

(65) Prior Publication Data
US 2021/0220492 A1    Jul. 22, 2021

(30) Foreign Application Priority Data

Jun. 15, 2017 (CN) .......................... 201710451094.8

(51) Int. Cl.
*A61K 51/04* (2006.01)
*C07H 23/00* (2006.01)

(52) U.S. Cl.
CPC .............................. *A61K 51/0491* (2013.01)

(58) Field of Classification Search
None
See application file for complete search history.

(56) References Cited

U.S. PATENT DOCUMENTS 4,735,793 A    4/1988    Jones et al.

FOREIGN PATENT DOCUMENTS

| CN | 102993243 A |   | 3/2013 |
| CN | 102146098 B | * | 8/2013 |
| CN | 107245087 A |   | 10/2017 |

OTHER PUBLICATIONS

Machine translation of CN-102146098-B, original document published Aug. 2013 (Year: 2013).*
CAPlus abstract of CN-102146098-B, original document published Aug. 2013 (Year: 2013).*
Schwochau K. Technetium radiopharmaceuticals—fundamentals, synthesis, structure, and development. Angewandte Chemie International Edition in English. Dec. 5, 1994;33(22):2258-67. (Year: 1994).*
Mizuno Y, Uehara T, Hanaoka H, Endo Y, Jen CW, Arano Y. Purification-free method for preparing technetium-99m-labeled multivalent probes for enhanced in vivo imaging of saturable systems. Journal of medicinal chemistry. Apr. 14, 2016;59(7):3331-9. (Year: 2016).*
Wang Y, Zhu J, Song X, Wang X, Yang J, Zhang J. Synthesis and evaluation of 99mTc-2-[(3-carboxy-1-oxopropyl) amino]-2-deoxy-D-glucose as a potential tumor imaging agent. Bioorganic & Medicinal Chemistry Letters. Aug. 15, 2014;24(16):3882-5. (Year: 2014).*
Zhang et al. "Evaluation of 99m Tc-CN5DG as a broad-spectrum SPECT probe for tumor imaging", Translational Oncology, 2021, 14, 100966.
International Search Report for International Application No. PCT/CN2018/073950, dated Apr. 23, 2018, 6 pages with English Translation.
International Written Opinion for International Application No. PCT/CN2018/073950, dated Jun. 21, 2018, 12 pages with English Translation.
Mizuno et al. "Correction to Purification-Free Method for Preparing Technetium-99m-Labeled Multivalent Probes for Enhanced in Vivo Imaging of Saturable Systems" Journal of Medicinal Chemistry (Mar. 2016) 59, 3331-3339.
Yang et al. "Imaging with 99m Tc ECDG Targeted at the Multifunctional Glucose Transport System: Feasibility Study with Rodents1" J. Radiology (Feb. 2003) vol. 226, No. 2, pp. 465-473.
Gan et al. "99mTc-CN7DG: A Highly Expected SPECT Imaging Agent of Cancer with Satisfactory Tumor Uptake and Tumor-to-Nontarget Ratios," Molecular Pharmaceutics, 18, (Feb. 2021) pp. 1356-1363.
Bryant et al. "99mTc-EC-DG: A novel tracer for tumor imaging" Journal of Clinical Oncology 2005 23:16_suppl, 2021-2021, https://ascopubs.org/doi/abs/10.1200/jco.2005.23.16_suppl.2021.
Shen et al. "The Evolving Role of 18F-FDG PET/CT in Diagnosis and Prognosis Prediction in Progressive Prostate Cancer" Front. Oncol., vol. 11, Article 683793 Jul. 29, 2021, https://doi.org/10.3389/fonc.2021.683793.
Xuran et al. et al. "Synthesis and biological evaluation of a 99mTc-labeled glucose derivative for tumor imaging" Chinese Science Chemistry, 52 pp. 963-971 (2022); doi: 10.1360/SSC-2021-0264 (Eng Abstract).

(Continued)

*Primary Examiner* — Nissa M Westerberg
(74) *Attorney, Agent, or Firm* — TraskBritt

(57) ABSTRACT

A $^{99m}$Tc-labeled isonitrile-containing glucose derivative having the general formula $[^{99m}$Tc-(CNDG)$_6]^+$, preparation method and use thereof is disclosed herein. The derivative is centered on $^{99m}$Tc$^+$, and the carbon atom of the isonitrile in CNDG coordinates with $^{99m}$Tc(I) to form a hexacoordinated complex $[^{99m}$Tc-(CNDG)$_6]^+$. The $[^{99m}$Tc-(CNDG)$_6]^+$ derivative was obtained by the synthesis of the ligand CNDG and the preparation of the lyophilized CNDG kit. The derivative of this disclosure has good stability, simple preparation, high uptake and good retention at a tumor site, and high tumor/non-target ratio, and it is a novel $^{99m}$Tc-labeled isonitrile-containing glucose derivative with excellent performance for tumor imaging. The derivative of this disclosure is advantageous for popularization and application.

2 Claims, No Drawings

(56) References Cited

OTHER PUBLICATIONS

Zhang et al. "Evaluation of 99mTc-CN5DG as a broad-spectrum SPECT probe for tumor imaging" Transl Oncol. Jan. 2021; 14(1): 100966.

* cited by examiner

$^{99m}$TC-LABELED ISONITRILE-CONTAINING GLUCOSE DERIVATIVE AND PREPARATION METHOD AND USE THEREOF

CROSS-REFERENCE TO RELATED APPLICATIONS

This application is a national phase entry under 35 U.S.C. § 371 of International Patent Application PCT/CN2018/073950, filed Jan. 24, 2018, designating the United States of America, which claims the benefit under Article 8 of the Patent Cooperation Treaty to Chinese Patent Application Serial No. CN201710451094.8, filed Jun. 15, 2017.

TECHNICAL FIELD

This disclosure relates to the technical field of radiopharmaceutical chemistry and clinical nuclear medicine and, in particular, relates to a $^{99m}$Tc-labeled isonitrile-containing glucose derivative and preparation method and use thereof.

BACKGROUND

At present, malignant tumors have become the first killer threatening human health and life in the field of clinical medicine. The annual incidence of tumors and mortality from tumors are still on the rise. Early diagnosis, early treatment and personalized treatment of tumors are the most effective measures for reducing mortality from tumors. Traditional non-invasive imaging methods for tumor detection, such as X-ray, CT and MM, are mainly morphological and structural imaging of organs under pathological conditions, while molecular imaging techniques of nuclear medicine, such as positron emission tomography (PET) and single photon emission computed tomography (SPECT), can reflect the changes of tumors in physiology, pathology, metabolism, and function at the molecular level. At present, with the organic fusion of imaging technologies, such as PET/CT, PET/MR and SPECT/CT, molecular imaging techniques play an increasingly important role in early diagnosis and personalized treatment of tumors. The study of radioactive molecular probes for tumors on which the molecular imaging technology of nuclear medicine depends, appears to be particularly urgent and important in order to adapt to the need for widespread application and rapid development of this technology in the clinical diagnosis and treatment fields.

At present, the tumor imaging agent that is most often used clinically is $^{18}$F-fluorodeoxyglucose ($^{18}$F-FDG). This imaging agent has good imaging effect, but its expensive diagnostic cost limits its wide application to a certain extent, especially in economically underdeveloped countries and regions, and is not widely used yet. Since $^{99m}$Tc has the advantages of suitable half-life ($T_{1/2}$=6.02 h) and γ single photon emission of 140 key, and the popularization and application of $^{99}$Mo-$^{99m}$Tc generator make $^{99m}$Tc radiopharmaceuticals more simple to prepare and capable of being contained in an inexpensive kit that is readily available and reliable in quality, the development of a new $^{99m}$Tc-labeled glucose-based tumor imaging agent with a clinical application value has important practical significance. Isonitriles are a class of organic compounds with the general formula of RNC, in which the nitrogen atom bears a part of positive charge and the carbon atom bears a part of negative charge. Studies have shown that the carbon atom in the isonitrile can coordinate with $^{99m}$Tc(I) to form a positive monovalent complex [$^{99m}$Tc-(CNR)$_6$]$^+$. $^{99m}$Tc-methoxyisobutylisonitrile ($^{99m}$Tc-MIBI) has been widely used clinically as an imaging agent for myocardium perfusion, and it has been found in clinics that the imaging agent has certain oncotropic effect. The isonitrile molecule connects $^{99m}$Tc and a sugar molecule in the tumor molecular probe of this disclosure, and functions as a bifunctional linker to integrate the function of oncotropic glucose metabolism with the tracer function of $^{99m}$Tc. Based on the above background, it is of great scientific significance and broad application prospect to develop and explore a $^{99m}$Tc-labeled glucose-based tumor molecular probe with excellent performance, convert glucosamine into an isonitrile-containing glucose derivative (referred to as CNDG) and then utilize the carbon atom in the isonitrile ligand to coordinate with $^{99m}$Tc, thereby obtaining a stable $^{99m}$Tc labeled isonitrile-containing glucose derivative used as a tumor imaging agent, also making it an important task in this field.

BRIEF SUMMARY

A $^{99m}$Tc-labeled isonitrile-containing glucose derivative that is stable and simple for preparation is disclosed herein. A method of preparation thereof is also disclosed.

This disclosure adopts the following technical solution: a $^{99m}$Tc-labeled isonitrile-containing glucose derivative having the structural formula of [$^{99m}$Tc-(CNDG)$_6$]$^+$ is shown as follows:

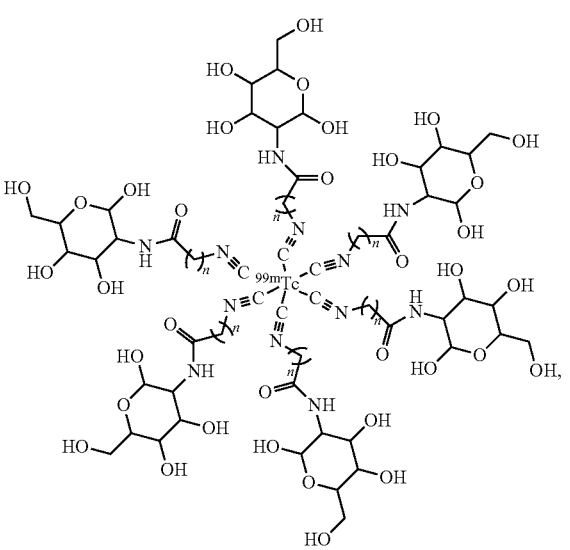

(I)

In the structural formula, a $^{99m}$Tc$^+$ core is taken as the central nucleus, the carbon atom of isonitrile in the CNDG coordinates with $^{99m}$Tc(I) to form a hexacoordinated complex [$^{99m}$Tc-(CNDG)$_6$]$^+$, and n is an integer in the range of 2 to 5.

The disclosure described herein provides a method for preparing the $^{99m}$Tc-labeled isonitrile-containing glucose derivative, wherein the preparation steps are as follows:

a: synthesis of the ligand CNDG:
The structural formula of compound (II) is as follows:

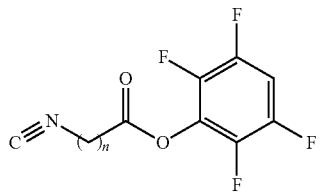
(II)

An appropriate amount of glucosamine hydrochloride is weighed in a 25 mL round bottom flask; anhydrous methanol is added for dissolving glucosamine hydrochloride; then an appropriate amount of NaOH is added. The reaction is performed at room temperature while stirring for 30 minutes. Then, the reaction flask is placed in an ice-water bath. An appropriate amount of methanol solution containing the compound (II) is slowly dropwise added while stirring. The reaction continues in ice-water bath for 3 hours after dropwise addition is completed. After the reaction is completed, the solvent is distilled off under reduced pressure, and the residues are purified by column chromatography (dichloromethane-methanol) to obtain the ligand CNDG.

A specific synthetic route is as follows:

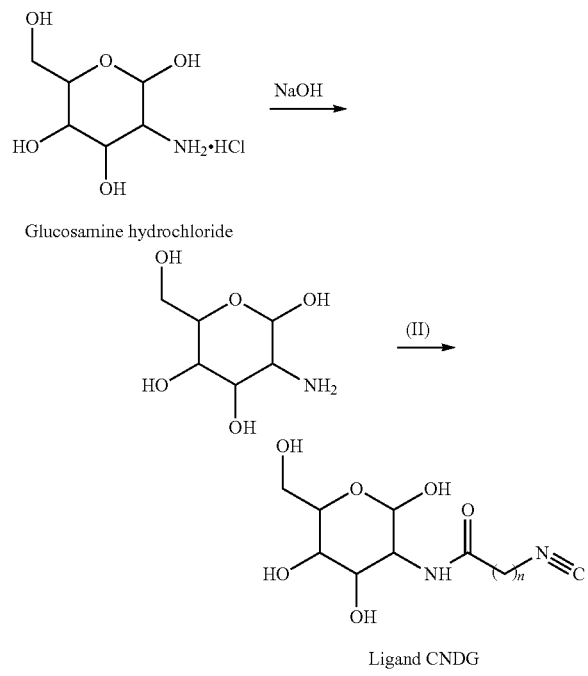

b: preparation of the complex $[^{99m}Tc\text{-}(CNDG)_6]^+$:
Preparation of lyophilized CNDG kit: CNDG, $SnCl_2 \cdot 2H_2O$ and sodium citrate are dissolved in an appropriate amount of redistilled water. The pH of the solution is adjusted to 5 to 6. Then, the solution is dispensed into clean penicillin vials in an amount of 1 mL after full dissolution, each vial containing 1.0 mg of CNDG, 0.03 mg of $SnCl_2 \cdot 2H_2O$ and an appropriate amount of sodium citrate, making the kit ready for use after lyophilization.

An appropriate amount of freshly washed $Na^{99m}TcO_4$ is added to the lyophilized CNDG kit, shaken well, and heated in a boiling water bath for 20 minutes after the solid was completely dissolved, to give the complex $[^{99m}Tc\text{-}(CNDG)_6]^+$.

The specific preparation steps are as follows:

1. Synthesis of CN2DG

Ninety-one mg (0.423 mmol) of glucosamine hydrochloride is weighed in a 25 mL round bottom flask, 3 ml of anhydrous methanol is added for dissolving, then 17 mg (0.423 mmol) of NaOH is added. The reaction is performed at room temperature while stirring for 30 minutes. Then, the reaction flask is placed in an ice-water bath. One ml of a methanol solution containing 114 mg (0.466 mmol) of the compound II (n=2) is slowly dropwise added while stirring. The reaction continues in an ice-water bath for 3 hours after dropwise addition is completed. After the reaction is completed, the solvent methanol is distilled off under reduced pressure, and the residual solid is separated and purified with a silica gel column (dichloromethane:methanol=5:1) and dried to obtain CN2DG;

2. Synthesis of CN3DG

One hundred seventeen mg (0.544 mmol) of glucosamine hydrochloride is weighed in a 25 mL round bottom flask. Three ml of anhydrous methanol is added for dissolving. Then, 22 mg (0.544 mmol) of NaOH is added. The reaction is performed at room temperature while stirring for 30 minutes. Then, the reaction flask is placed in an ice-water bath. One ml of a methanol solution containing 156 mg (0.598 mmol) of the compound II (n=3) is slowly dropwise added while stirring. The reaction continues in an ice-water bath for 3 hours after dropwise addition is completed. After the reaction is completed, the solvent methanol is distilled off under reduced pressure, and the residual solid is separated and purified with a silica gel column (dichloromethane:methanol=5:1) and dried to obtain CN3DG.

3. Synthesis of CN4DG

One hundred twenty-nine mg (0.600 mmol) of glucosamine hydrochloride is weighed in a 25 mL round bottom flask. Three ml of anhydrous methanol is added for dissolving, then 24 mg (0.600 mmol) of NaOH is added. The reaction is performed at room temperature while stirring for 30 minutes. Then, the reaction flask is placed in an ice-water bath. One ml of a methanol solution containing 182 mg (0.660 mmol) of the compound II (n=4) in methanol is slowly dropwise added while stirring. The reaction continues in an ice-water bath for 3 hours after dropwise addition is completed. After the reaction is completed, the solvent methanol is distilled off under reduced pressure, and the residual solid is separated and purified with a silica gel column (dichloromethane:methanol=5:1) and dried to obtain CN4DG.

4. Synthesis of CN5DG

One hundred forty-seven mg (0.684 mmol) of glucosamine hydrochloride is weighed in a 25 mL round bottom flask. Three ml of anhydrous methanol is added for dissolving, then 27 mg (0.684 mmol) of NaOH is added. The reaction is performed at room temperature while stirring for 30 minutes. Then, the reaction flask is placed in an ice-water bath. One ml of a methanol solution containing 217 mg (0.752 mmol) of the compound II (n=5) is slowly dropwise added while stirring. The reaction continues in an ice-water bath for 3 hours after dropwise addition is completed. After the reaction is completed, the solvent methanol is distilled off under reduced pressure, and the residual solid is separated and purified with a silica gel column (dichloromethane:methanol=5:1) and dried to obtain CN5DG.

5. Synthesis of $[^{99m}Tc\text{-}(CN2DG)_6]^+$, $[^{99m}Tc\text{-}(CN3DG)_6]^+$, $[^{99m}Tc\text{-}(CN4DG)_6]^+$ and $[^{99m}Tc\text{-}(CN5DG)_6]^+$ Preparation of lyophilized CN2DG kit: CN2DG, $SnCl_2 \cdot 2H_2O$ and sodium citrate are dissolved in an appropriate amount of redistilled water. pH of the solution is adjusted to 5 to 6, then dispensed into clean penicillin vials in an amount of 1 mL after full dissolution, each vial containing 1.0 mg of CN2DG, 0.03 mg of $SnCl_2 \cdot 2H_2O$ and an appropriate amount of sodium citrate. The kit is ready for use after lyophilization.

One mL to 5 mL of freshly washed $Na^{99m}TcO_4$ is added to the lyophilized CN2DG kit, shaken well, and heated in a boiling water bath for 20 minutes after the solid was completely dissolved, to result in the complex $[^{99m}Tc\text{-}(CN2DG)_6]^+$.

Preparation of lyophilized CN3DG kit: CN3DG, $SnCl_2 \cdot 2H_2O$ and sodium citrate are dissolved in an appropriate amount of redistilled water. pH of the solution is adjusted to 5 to 6, then the resultant solution is dispensed into clean penicillin vials in an amount of 1 mL after full dissolution, each vial containing 1.0 mg of CN3DG, 0.03 mg of $SnCl_2 \cdot 2H_2O$ and an appropriate amount of sodium citrate. The kit is ready for use after lyophilization.

One mL to 5 mL of freshly washed $Na^{99m}TcO_4$ is added to the lyophilized CN3DG kit, shaken well, and heated in a boiling water bath for 20 minutes after the solid was completely dissolved, resulting in the complex $[^{99m}Tc\text{-}(CN3DG)_6]^+$.

Preparation of lyophilized CN4DG kit: CN4DG, $SnCl_2 \cdot 2H_2O$ and sodium citrate are dissolved in an appropriate amount of redistilled water. pH of the solution is adjusted to 5 to 6, then the resultant solution is dispensed into clean penicillin vials in an amount of 1 mL after full dissolution, each vial containing 1.0 mg of CN4DG, 0.03 mg of $SnCl_2 \cdot 2H_2O$ and an appropriate amount of sodium citrate. The kit is ready for use after lyophilization.

One mL to 5 mL of freshly washed $Na^{99m}TcO_4$ is added to the lyophilized CN4DG kit, shaken well, and heated in a boiling water bath for 20 minutes after the solid was completely dissolved, resulting in the complex $[^{99m}Tc\text{-}(CN4DG)_6]^+$.

Preparation of lyophilized CN5DG kit: CN5DG, $SnCl_2 \cdot 2H_2O$ and sodium citrate are dissolved in an appropriate amount of redistilled water. pH of the solution is adjusted to 5 to 6, then the resultant solution is dispensed into clean penicillin vials in an amount of 1 mL after full dissolution, each vial containing 1.0 mg of CN5DG, 0.03 mg of $SnCl_2 \cdot 2H_2O$ and an appropriate amount of sodium citrate. The kit is ready for use after lyophilization.

One mL to 5 mL of freshly washed $Na^{99m}TcO_4$ is added to the lyophilized CN5DG kit, shaken well, and heated in a boiling water bath for 20 minutes after the solid was completely dissolved, to result in the complex $[^{99m}Tc\text{-}(CN5DG)_6]^+$.

The reagent raw materials used in the chemical synthesis of this disclosure are all commercially available products and have a wide range of sources. The complex $[^{99m}Tc\text{-}(CNDG)_6]^+$ prepared by the above method has a radiochemical purity of greater than 90%, is a hydrophilic substance, and has good in vitro stability. It has high uptake and good retention at the tumor sites of tumor-bearing mice, good tumor/muscle ratio and tumor/blood ratio, and low uptake value in non-target organs such as liver, kidney and lung, and is a novel $^{99m}Tc$-labeled isonitrile-containing glucose derivative with excellent performance that can be used for tumor imaging.

Determination of the performance of the $[^{99m}Tc\text{-}(CNDG)_6]^+$ of this disclosure:

1. Chromatographic Identification of the Complex $[^{99m}Tc\text{-}(CNDG)_6]^+$

The radiochemical purity of the labeled substance is identified by thin layer chromatography (TLC). The developing system used is a methanol/polyamide film sheet. Under this system, the Rf values of the radioactive component are shown in the following table.

|    | $^{99m}TcO_4^-$ | $^{99m}TcO_2 \cdot nH_2O$ | $[^{99m}Tc\text{-}(CNDG)_6]^+$ |
|----|-----------------|---------------------------|-------------------------------|
| Rf | 0–0.1           | 0–0.1                     | 0.7–1.0                       |

The radiochemical purities of the labeled substances as determined by the above chromatographic identification are all greater than 90%.

2. Determination of the Lipid-Water Partition Coefficient

One hundred μL of the labeled substance solution (50 μCi) diluted with normal saline is placed into a 2 mL centrifuge tube, and then 800 μL of n-octanol and 700 μL of PBS are added to the centrifuge tube, which is subsequently covered with a cap. The centrifuge tube is vortexed for 3 minutes (2500 r/minute), allowed to stand until the solution is layered, and centrifuged in a centrifuge for 3 minutes (3000 r/minute). Three samples of the upper organic phase and three samples of the lower aqueous phase are taken, each 100 μL, and detected in a γ-counter for the radioactive counts of the organic and aqueous phases, respectively. The lipid-water partition coefficient P=the radioactive count of the organic phase/the radioactive count of the water phase, and the lipid-water partition coefficient is usually represented by Log P. The Log P values of $[^{99m}Tc\text{-}(CN2DG)_6]^+$, $[^{99m}Tc\text{-}(CN3DG)_6]^+$, $[^{99m}Tc\text{-}(CN4DG)_6]^+$ and $[^{99m}Tc\text{-}(CN5DG)_6]^+$ are determined to be $-4.26\pm0.12$, $-4.01\pm0.17$, $-3.84\pm0.06$ and $-3.57\pm0.35$, respectively, indicating that the labeled substances are all water-soluble substances and the hydrophilic performance of the corresponding labeled substances decreases as the value of n increases.

3. Determination of the Stability

The radiochemical purities of the labeled substances are determined after the labeled substances are kept at room temperature and at 37° C. in mouse serum for different time periods (1, 2, 3, and 4 hours), respectively. The test results show that all the radiochemical purities are greater than 90% after the labeled substances are kept at room temperature and at 37° C. in mouse serum for 4 hours, indicating that the labeled substances have good in vitro stability.

4. Determination of the Bio-Distribution in Tumor-Bearing Mice

The labeled solution (0.1 mL, 74 KBq) is injected into mice through the tail vein, and the injection time is recorded. Then the mice were killed by cervical dislocation at different time phases (30 minutes, 60 minutes, and 120 minutes), five mice for each time phase, and the organs of interest such as heart, liver, lung, kidney, spleen, stomach, muscle, blood and tumor are taken out after dissection, and measured with a γ-counter for the radioactive count of each organ. The uptake value of each organ is obtained by calculation based on the mass of the organ (with % ID/g as the unit). The bio-distribution results of each labeled substance in tumor-bearing mice are shown in Tables 1 to 4:

TABLE 1

Bio-distribution results of [$^{99m}$Tc-(CN2DG)$_6$]$^+$
in S180-bearing mice (x ± s, % ID/g)

| Organs | 30 min | 60 min | 120 min |
| --- | --- | --- | --- |
| Heart | 0.34 ± 0.06 | 0.12 ± 0.02 | 0.05 ± 0.02 |
| Liver | 0.35 ± 0.06 | 0.18 ± 0.02 | 0.09 ± 0.01 |
| Lung | 0.94 ± 0.18 | 0.26 ± 0.06 | 0.09 ± 0.04 |
| Kidney | 3.11 ± 1.04 | 1.17 ± 0.27 | 0.68 ± 0.11 |
| Spleen | 0.31 ± 0.09 | 0.13 ± 0.02 | 0.07 ± 0.01 |
| Stomach | 0.38 ± 0.15 | 0.19 ± 0.07 | 0.15 ± 0.06 |
| Bone | 0.32 ± 0.07 | 0.10 ± 0.02 | 0.05 ± 0.02 |
| Muscle | 0.27 ± 0.07 | 0.08 ± 0.00 | 0.04 ± 0.01 |
| Small intestine | 0.44 ± 0.16 | 0.19 ± 0.03 | 0.12 ± 0.02 |
| Tumor | 1.09 ± 0.23 | 0.50 ± 0.07 | 0.25 ± 0.05 |
| Blood | 0.94 ± 0.18 | 0.20 ± 0.05 | 0.01 ± 0.00 |
| Tumor/muscle | 4.04 | 6.25 | 6.25 |
| Tumor/blood | 1.16 | 2.78 | 25.00 |

TABLE 2

Bio-distribution results of [$^{99m}$Tc-(CN3DG)$_6$]$^+$
in S180-bearing mice (x ± s, % ID/g)

| Organs | 30 min | 60 min | 120 min |
| --- | --- | --- | --- |
| Heart | 0.40 ± 0.07 | 0.22 ± 0.04 | 0.22 ± 0.05 |
| Liver | 0.39 ± 0.12 | 0.23 ± 0.03 | 0.28 ± 0.04 |
| Lung | 0.78 ± 0.12 | 0.23 ± 0.04 | 0.17 ± 0.05 |
| Kidney | 2.17 ± 0.43 | 1.05 ± 0.21 | 1.23 ± 0.26 |
| Spleen | 0.28 ± 0.05 | 0.15 ± 0.03 | 0.17 ± 0.06 |
| Stomach | 0.64 ± 0.25 | 0.25 ± 0.07 | 0.31 ± 0.06 |
| Bone | 0.27 ± 0.05 | 0.15 ± 0.02 | 0.13 ± 0.04 |
| Muscle | 0.37 ± 0.08 | 0.17 ± 0.07 | 0.17 ± 0.05 |
| Small intestine | 0.44 ± 0.08 | 0.21 ± 0.14 | 0.14 ± 0.06 |
| Tumor | 1.49 ± 0.08 | 1.00 ± 0.17 | 0.68 ± 0.23 |
| Blood | 0.78 ± 0.16 | 0.12 ± 0.03 | 0.04 ± 0.02 |
| Tumor/muscle | 4.03 | 5.88 | 4.00 |
| Tumor/blood | 1.91 | 8.33 | 17.00 |

TABLE 3

Bio-distribution results of [$^{99m}$Tc-(CN4DG)$_6$]$^+$
in S180-bearing mice (x ± s, % ID/g)

| Organs | 30 min | 60 min | 120 min |
| --- | --- | --- | --- |
| Heart | 0.70 ± 0.18 | 0.22 ± 0.08 | 0.10 ± 0.04 |
| Liver | 0.66 ± 0.13 | 0.28 ± 0.06 | 0.17 ± 0.03 |
| Lung | 1.75 ± 0.49 | 0.40 ± 0.11 | 0.13 ± 0.02 |
| Kidney | 4.93 ± 1.11 | 1.57 ± 0.27 | 1.24 ± 0.53 |
| Spleen | 0.53 ± 0.12 | 0.21 ± 0.04 | 0.11 ± 0.02 |
| Stomach | 0.81 ± 0.33 | 0.23 ± 0.07 | 0.08 ± 0.01 |
| Bone | 0.73 ± 0.23 | 0.19 ± 0.04 | 0.13 ± 0.09 |
| Muscle | 0.57 ± 0.18 | 0.27 ± 0.17 | 0.15 ± 0.07 |
| Small intestine | 1.06 ± 0.33 | 0.25 ± 0.11 | 0.36 ± 0.21 |
| Tumor | 1.72 ± 0.30 | 0.88 ± 0.09 | 0.45 ± 0.17 |
| Blood | 1.80 ± 0.53 | 0.30 ± 0.13 | 0.03 ± 0.01 |
| Tumor/muscle | 3.01 | 3.26 | 3.00 |
| Tumor/blood | 0.95 | 2.93 | 15.00 |

TABLE 4

Bio-distribution results of [$^{99m}$Tc-(CN5DG)$_6$]$^+$
in S180-bearing mice (x ± s, % ID/g)

| Organs | 30 min | 60 min | 120 min |
| --- | --- | --- | --- |
| Heart | 0.64 ± 0.12 | 0.41 ± 0.02 | 0.22 ± 0.04 |
| Liver | 0.61 ± 0.07 | 0.38 ± 0.08 | 0.34 ± 0.08 |
| Lung | 1.58 ± 0.18 | 0.59 ± 0.16 | 0.29 ± 0.06 |
| Kidney | 4.69 ± 0.76 | 2.68 ± 0.32 | 2.07 ± 0.13 |
| Spleen | 0.51 ± 0.08 | 0.28 ± 0.07 | 0.17 ± 0.02 |
| Stomach | 0.50 ± 0.09 | 0.37 ± 0.14 | 0.35 ± 0.06 |
| Bone | 0.72 ± 0.11 | 0.41 ± 0.15 | 0.15 ± 0.04 |
| Muscle | 0.46 ± 0.05 | 0.27 ± 0.10 | 0.18 ± 0.03 |
| Small intestine | 0.74 ± 0.09 | 0.43 ± 0.07 | 0.22 ± 0.08 |
| Tumor | 1.83 ± 0.18 | 1.07 ± 0.21 | 0.75 ± 0.07 |
| Blood | 1.58 ± 0.15 | 0.55 ± 0.17 | 0.16 ± 0.02 |
| Tumor/muscle | 3.98 | 3.96 | 4.16 |
| Tumor/blood | 1.16 | 1.94 | 4.69 |

The bio-distribution data of [$^{99m}$Tc-(CN2DG)$_6$]$^+$, [$^{99m}$Tc-(CN3DG)$_6$]$^+$, [$^{99m}$Tc-(CN4DG)$_6$]$^+$ and [$^{99m}$Tc-(CN5DG)$_6$]$^+$ in tumor-bearing mice are compared with that of $^{99m}$Tc-ECDG, which has entered the phase III clinical study (J. David et al., Imaging with $^{99m}$Tc-ECDG Targeted at the Multifunctional Glucose Transport System: Feasibility Study with Rodents, *J. Radiology* 2003, 226(2):465-473), and the results are shown in Table 5.

TABLE 5

Data comparison between bio-distribution of [$^{99m}$Tc-(CN2DG)$_6$]$^+$,
[$^{99m}$Tc-(CN3DG)$_6$]$^+$, [$^{99m}$Tc-(CN4DG)$_6$]$^+$, [$^{99m}$Tc-(CN5DG)$_6$]$^+$ and
$^{99m}$Tc-ECDG (% ID/g) in tumor-bearing mice 0.5 hour after injection

| | [$^{99m}$Tc-(CN2DG)$_6$]$^+$ | [$^{99m}$Tc-(CN3DG)$_6$]$^+$ | [$^{99m}$Tc-(CN4DG)$_6$]$^+$ | [$^{99m}$Tc-(CN5DG)$_6$]$^+$ | $^{99m}$Tc-ECDG |
| --- | --- | --- | --- | --- | --- |
| Liver | 0.35 ± 0.06 | 0.39 ± 0.12 | 0.66 ± 0.13 | 0.61 ± 0.07 | 5.67 ± 2.08 |
| Kidney | 3.11 ± 1.04 | 2.17 ± 0.43 | 4.93 ± 1.11 | 4.69 ± 0.76 | 6.73 ± 1.84 |
| Tumor | 1.09 ± 0.23 | 1.49 ± 0.08 | 1.72 ± 0.30 | 1.83 ± 0.18 | 0.79 ± 0.16 |
| Muscle | 0.27 ± 0.07 | 0.37 ± 0.08 | 0.57 ± 0.18 | 0.46 ± 0.05 | 0.26 ± 0.07 |
| Blood | 0.94 ± 0.18 | 0.78 ± 0.16 | 1.80 ± 0.53 | 1.58 ± 0.15 | 1.61 ± 0.39 |
| Tumor/muscle | 4.04 | 4.03 | 3.01 | 3.98 | 3.04 |
| Tumor/blood | 1.16 | 1.91 | 0.95 | 1.16 | 0.49 |
| Tumor/liver | 3.11 | 3.82 | 2.60 | 3.00 | 0.14 |

The above results show that [$^{99m}$Tc-(CN2DG)$_6$]$^+$, [$^{99m}$Tc-(CN3DG)$_6$]$^+$, [$^{99m}$Tc-(CN4DG)$_6$]$^+$ and [$^{99m}$Tc-(CN5DG)$_6$]$^+$ are superior to $^{99m}$Tc-ECDG in the uptake in tumors, the tumor/blood ratio, and tumor/liver ratio, and the uptake values thereof in liver, kidney and other organs are lower than $^{99m}$Tc-ECDG. Therefore, [$^{99m}$Tc-(CN2DG)$_6$]$^+$, [$^{99m}$Tc-(CN3DG)$_6$]$^+$, [$^{99m}$Tc-(CN4DG)$_6$]$^+$ and [$^{99m}$Tc-(CN5DG)$_6$]$^+$ can be popularized and applied as a novel tumor imaging agent with excellent performance.

5. Determination by SPECT Imaging

The prepared [$^{99m}$Tc-(CN3DG)$_6$]$^+$ or [$^{99m}$Tc-(CN5DG)$_6$]$^+$ (0.2 mL, 700 μCi) is injected into tumor-bearing mice through tail vein, and SPECT imaging is performed 1 hour later. The SPECT imaging results show that both of them have evident aggregation at the tumor sites, and also have a relatively high concentration in kidney, while the uptake thereof in other organs is relatively low, indicating that they can be tumor imaging agents with excellent performance.

DETAILED DESCRIPTION

This disclosure will be described in detail below by way of Examples: $^{99m}$Tc-labeled isonitrile-containing glucose derivatives having the structural formula of [$^{99m}$Tc-(CNDG)$_6$]$^+$, which are prepared by the following steps:

a: synthesis of the ligand CNDG:

An appropriate amount of glucosamine hydrochloride was weighed in a 25 mL round bottom flask. Anhydrous methanol was added for dissolving. Then, an appropriate amount of NaOH was added, and the reaction was performed at room temperature while stirring for 30 minutes. Then, the reaction flask was placed in an ice-water bath. An appropriate amount of a methanol solution of compound (II) was slowly dropwise added while stirring. The reaction continued in ice-water bath for 3 hours after dropwise addition was completed. After the reaction was completed, the solvent was distilled off under reduced pressure, and the residues were purified by column chromatography (dichloromethane-methanol) to obtain the ligand CNDG.

The specific synthetic route was as follows:

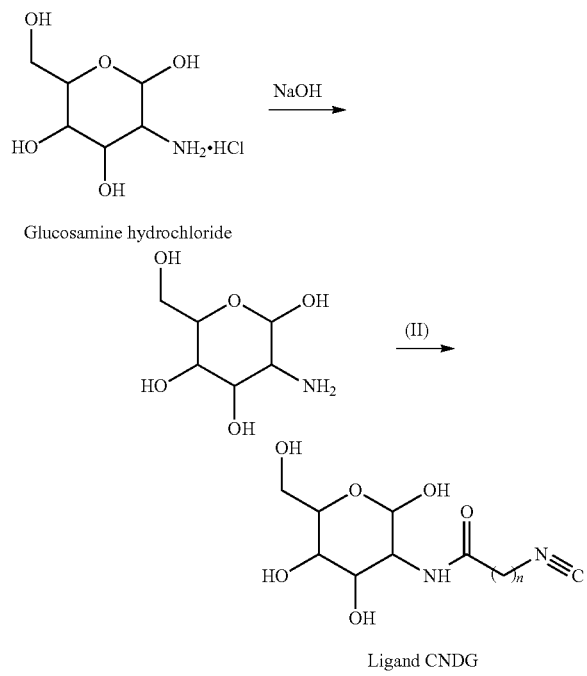

b: preparation of the complex [$^{99m}$Tc-(CNDG)$_6$]$^+$, the specific preparation steps were as follows:

1. Synthesis of CN2DG

Ninety-one mg (0.423 mmol) of glucosamine hydrochloride was weighed in a 25 mL round bottom flask. Three ml of anhydrous methanol was added for dissolving, then 17 mg (0.423 mmol) of NaOH was added. The reaction was performed at room temperature while stirring for 30 minutes. Then, the reaction flask was placed in an ice-water bath. One ml of a methanol solution containing 114 mg (0.466 mmol) of the compound II (n=2) was slowly dropwise added while stirring. The reaction continued in an ice-water bath for 3 hours after dropwise addition was completed. After the reaction was completed, the solvent methanol was distilled off under reduced pressure, and the residual solid was separated and purified with a silica gel column (dichloromethane:methanol=5:1) and dried to obtain the product CN2DG, 83 mg, 75% yield. $^1$H-NMR (400 MHz, D$_2$O): δ (ppm) 3.65-3.89 (m, 7H), 3.34-3.44 (m, 2H), 2.65 (t, 2H). HRMS Calculated for, C$_{10}$H$_{16}$N$_2$O$_6$Na [M+Na]$^+$283.0911, found 283.0906. IR (KBr)/cm$^{-1}$: 3303.24 (—OH), 2933.85, 2149.76 (—NC), 1647.28 (—C=O), 1560.48, 1303.03, 586.39.

2. Synthesis of CN3DG

One hundred seventeen mg (0.544 mmol) of glucosamine hydrochloride was weighed in a 25 mL round bottom flask. Three ml of anhydrous methanol was added for dissolving, then 22 mg (0.544 mmol) of NaOH was added. The reaction was performed at room temperature while stirring for 30 minutes. Then, the reaction flask was placed in an ice-water bath. One ml of a methanol solution containing 156 mg (0.598 mmol) of the compound II (n=3) was slowly dropwise added while stirring. The reaction continued in an ice-water bath for 3 hours after dropwise addition was completed. After the reaction was completed, the solvent methanol was distilled off under reduced pressure, and the residual solid was separated and purified with a silica gel column (dichloromethane:methanol=5:1) and dried to obtain the product CN3DG, 85 mg, 57% yield. $^1$H-NMR (400 MHz, D$_2$O): δ (ppm) 3.65-3.85 (m, 5H), 3.42-3.49 (m, 4H), 2.37-2.42 (m, 2H), 2.19 (t, 2H). HRMS Calculated for C$_{11}$H$_{18}$N$_2$O$_6$Na [M+Na]$^+$, 297.1057, found, 297.1052. IR (KBr)/cm$^{-1}$: 3299.38 (—OH), 2932.89, 2149.76 (—NC), 1647.28 (—C=O), 1558.55, 1303.03, 588.31.

3. Synthesis of CN4DG

One hundred twenty-nine mg (0.600 mmol) of glucosamine hydrochloride was weighed in a 25 mL round bottom flask. Three ml of anhydrous methanol was added for dissolving, then 24 mg (0.600 mmol) of NaOH was added. The reaction was performed at room temperature while stirring for 30 minutes. Then, the reaction flask was placed in an ice-water bath, 1 ml of a methanol solution containing 182 mg (0.660 mmol) of the compound II (n=4) was slowly dropwise added while stirring. The reaction continued in the ice-water bath for 3 hours after dropwise addition was completed. After the reaction was completed, the solvent methanol was distilled off under reduced pressure, and the residual solid was separated and purified with a silica gel column (dichloromethane:methanol=5:1) and dried to obtain the product CN4DG, 108 mg, 63% yield. $^1$H-NMR (400 MHz, D$_2$O): δ (ppm) 3.65-3.89 (m, 5H), 3.38-3.44 (m, 4H), 2.28 (t, 2H), 1.60-1.75 (m, 4H). HRMS Calculated for C$_{12}$H$_{21}$N$_2$O$_6$ [M+H]$^+$, 289.1394, found 289.1396. IR (KBr)/cm$^{-1}$: 3295.52 (—OH), 2943.50, 2150.72 (—NC), 1645.35 (—C=O), 1542.15, 1093.69, 1033.89, 599.89.

4. Synthesis of CN5DG

One hundred forty-seven mg (0.684 mmol) of glucosamine hydrochloride was weighed in a 25 mL round bottom flask. Three ml of anhydrous methanol was added for dissolving, then 27 mg (0.684 mmol) of NaOH was added. The reaction was performed at room temperature while stirring for 30 minutes. Then, the reaction flask was placed in an ice-water bath, 1 ml of a methanol solution containing 217 mg (0.752 mmol) of the compound II (n=5) was slowly dropwise added while stirring. The reaction continued in the ice-water bath for 3 hours after dropwise addition was completed. After the reaction was completed, the solvent methanol was distilled off under reduced pressure, and the residual solid was separated and purified with a silica gel column (dichloromethane:methanol=5:1) and dried to obtain the product CN5DG 161 mg, yield 78%. $^1$H-NMR (400 MHz, $D_2O$): δ (ppm) 3.74-3.82 (m, 3H), 3.63-3.70 (m, 2H), 3.34-3.40 (m, 4H), 2.24 (q, 2H), 1.53-1.59 (m, 4H), 1.33-1.38 (m, 2H). HRMS Calculated for $C_{13}H_{22}N_2O_6Na$ [M+Na]$^+$, 325.1374, found 325.1370. IR (KBr)/cm$^{-1}$: 3294.56 (—OH), 2941.57, 2148.79 (—NC), 1645.35 (—C=O), 1538.30, 1093.69, 1032.93, 590.85.

5. Synthesis of [$^{99m}$Tc-(CN2DG)$_6$]$^+$, [$^{99m}$Tc-(CN3DG)$_6$]$^+$, [$^{99m}$Tc-(CN4DG)$_6$]$^+$ and [$^{99m}$Tc-(CN5DG)$_6$]$^+$ Preparation of lyophilized CN2DG kit: CN2DG, $SnCl_2.2H_2O$ and sodium citrate were dissolved in an appropriate amount of redistilled water, and pH of the solution was adjusted to 5 to 6. Then, the resultant solution was dispensed into clean penicillin vials in an amount of 1 mL after full dissolution, each vial containing 1.0 mg of CN2DG, 0.03 mg of $SnCl_2.2H_2O$ and an appropriate amount of sodium citrate. The kit was ready for use after lyophilization.

One to 5 mL of freshly washed Na$^{99m}$TcO$_4$ was added to the lyophilized CN2DG kit, shaken well, and heated in a boiling water bath for 20 minutes after the solid was completely dissolved, resulting in the complex [$^{99m}$Tc-(CN2DG)$_6$]$^+$.

Preparation of lyophilized CN3DG kit: CN3DG, $SnCl_2.2H_2O$ and sodium citrate were dissolved in an appropriate amount of redistilled water, and pH of the solution was adjusted to 5 to 6. Then, the resultant solution was dispensed into clean penicillin vials in an amount of 1 mL after full dissolution, each vial containing 1.0 mg of CN3DG, 0.03 mg of $SnCl_2.2H_2O$ and an appropriate amount of sodium citrate. The kit was ready for use after lyophilization.

One to 5 mL of freshly washed Na$^{99m}$TcO$_4$ was added to the lyophilized CN3DG kit, shaken well, and heated in a boiling water bath for 20 minutes after the solid was completely dissolved, resulting in the complex [$^{99m}$Tc-(CN3DG)$_6$]$^+$.

Preparation of lyophilized CN4DG kit: CN4DG, $SnCl_2.2H_2O$ and sodium citrate were dissolved in an appropriate amount of redistilled water, and pH of the solution was adjusted to 5 to 6. Then, the resultant solution was dispensed into clean penicillin vials in an amount of 1 mL after full dissolution, each vial containing 1.0 mg of CN4DG, 0.03 mg of $SnCl_2.2H_2O$ and an appropriate amount of sodium citrate. The kit was ready for use after lyophilization.

One to 5 mL of freshly washed Na$^{99m}$TcO$_4$ was added to the lyophilized CN4DG kit, shaken well, and heated in a boiling water bath for 20 minutes after the solid was completely dissolved, resulting in the complex [$^{99m}$Tc-(CN4DG)$_6$]$^+$.

Preparation of lyophilized CN5DG kit: CN5DG, $SnCl_2.2H_2O$ and sodium citrate were dissolved in an appropriate amount of redistilled water, and pH of the solution was adjusted to 5 to 6. Then, the resultant solution was dispensed into clean penicillin vials in an amount of 1 mL after full dissolution, each vial containing 1.0 mg of CN5DG, 0.03 mg of $SnCl_2.2H_2O$ and an appropriate amount of sodium citrate. The kit was ready for use after lyophilization.

One to 5 mL of freshly washed Na$^{99m}$TcO$_4$ was added to the lyophilized CN5DG kit, shaken well, and heated in a boiling water bath for 20 minutes after the solid was completely dissolved, resulting in the complex [$^{99m}$Tc-(CN5DG)$_6$]$^+$.

Use of the $^{99m}$Tc-labeled isonitrile-containing glucose derivative as described above as a tumor imaging agent in the field of nuclear medicine.

The above-described Examples are merely illustrative of the disclosure, but not intended to limit the scope of the disclosure.

INDUSTRIAL APPLICABILITY

This disclosure provides a $^{99m}$Tc labeled isonitrile-containing glucose derivative having the general formula of [$^{99m}$Tc-(CNDG)$_6$]$^+$, preparation method and use thereof. This derivative is centered on $^{99m}$Tc$^+$, and the carbon atom of isonitrile in CNDG coordinates with $^{99m}$Tc(I) to form a hexacoordinated complex [$^{99m}$Tc-(CNDG)$_6$]$^+$. The derivative provided by this disclosure has good stability, simple preparation, high uptake and good retention at tumor sites, and high tumor/non-target ratio, and it is a novel $^{99m}$Tc labeled isonitrile-containing glucose derivative with excellent performance for tumor imaging. The derivative provided by this disclosure is advantageous for popularization and application, and has high economic value and good application prospects.

What is claimed is:

1. A $^{99m}$Tc-labeled isonitrile-containing glucose derivative having a structural formula (I) of [$^{99m}$Tc-(CNDG)$_6$]$^+$, wherein structural formula (I) is shown as follows:

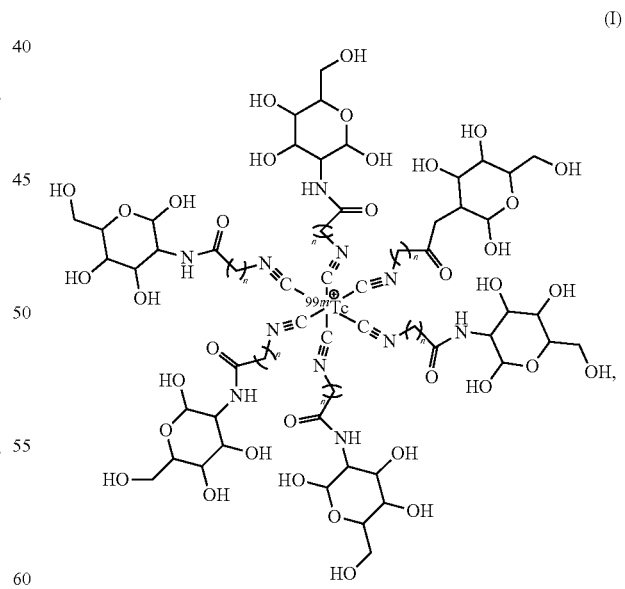

(I)

wherein, in the structural formula, a $^{99m}$Tc$^+$ core is taken as the central nucleus (I), the carbon atom of isonitrile in the CNDG coordinates with $^{99m}$Tc(I) to form a hexacoordinated complex [$^{99m}$Tc-(CNDG)$_6$]$^+$, and n is an integer greater than two (2).

2. A method of preparing a $^{99m}$Tc-labeled isonitrile-containing glucose derivative ("CNDG") having a structural formula (I) of $[^{99m}$Tc-(CNDG)$_6]^+$, wherein formula (I) is as follows:

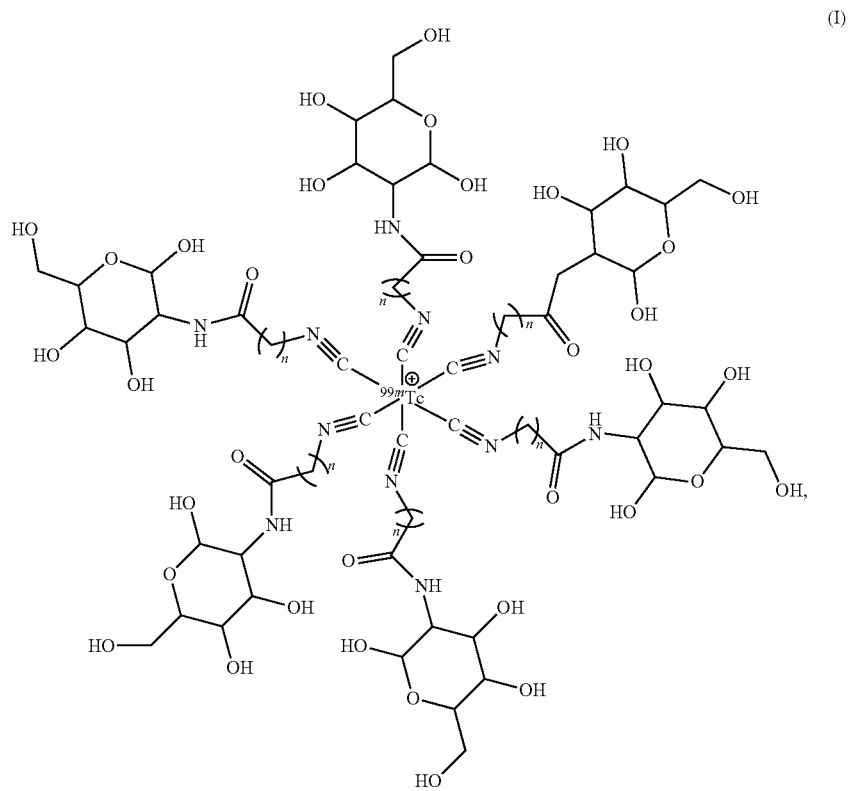

(I)

wherein, in the structural formula (I),
  a $^{99m}$Tc$^+$ core is a central nucleus,
  the carbon atom of isonitrile in the CNDG coordinates with $^{99m}$Tc(I) to form a hexacoordinated complex $[^{99m}$Tc-(CNDG)$_6]^+$, and
  n is an integer greater than two (2),
the method comprising:
  (a) synthesizing a CNDG ligand by a method comprising:
    weighing an appropriate amount of glucosamine hydrochloride;
    adding anhydrous methanol to dissolve glucosamine hydrochloride to produce a methanol solution;
    adding an appropriate amount of NaOH;
    allowing a reaction between NaOH and glucosamine hydrochloride to proceed at room temperature for about 30 minutes;
    placing the reaction in an ice water bath;
    adding a methanol solution comprising a compound of structural formula (II) dropwise to the reaction in the ice water bath for three hours after addition is completed to produce the CNDG ligand, the compound of the structural formula (II) as follows:

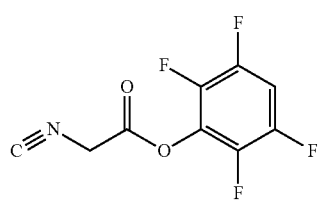

(II)

wherein n is an integer greater than two (2); and
    removing the solvent from the CNDG ligand upon completion of the reaction;
  (b) producing a solution of CNDG ligand, SnCl$_2$.2H$_2$O and sodium citrate dissolved in redistilled water, wherein a pH of the solution is adjusted to a pH from 5 to 6 after dissolution, wherein an appropriate volume of the solution is dispensed into a receptacle;
  (c) lyophilizing the solution in the receptacle to produce a lyophilized CNDG kit;
  (d) adding freshly washed Na$^{99m}$TcO$_4$ to the lyophilized CNDG kit; and
  (e) heating the solution containing the CNDG kit contents and Na$^{99m}$TcO$_4$ to produce the $[^{99m}$Tc-(CNDG)$_6]^+$.

* * * * *